United States Patent [19]
Yang et al.

[11] Patent Number: 6,140,107
[45] Date of Patent: *Oct. 31, 2000

[54] ORGANOMETALLIC-METABOLIZING YEAST

[75] Inventors: Ping Yang, Fullerton; Houn Simon Hsia, Foothill Ranch, both of Calif.

[73] Assignee: Viva America Marketing, Inc., Costa Mesta, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,572

[22] Filed: Sep. 25, 1996

[51] Int. Cl.⁷ .............................. C12N 1/14; C12N 1/16
[52] U.S. Cl. .................................. 435/255.2; 435/255.1; 435/940
[58] Field of Search ............................. 435/255.1, 255.2, 435/940

[56] References Cited

U.S. PATENT DOCUMENTS 4,530,846  7/1985  Nagodawithana et al. ............... 426/62

FOREIGN PATENT DOCUMENTS

| 3345211 | 6/1985 | Germany . |
| 53-127882 | 11/1978 | Japan . |
| 53-130483 | 11/1978 | Japan . |

OTHER PUBLICATIONS

Barnett J.A. et al. Yeasts Characteristics abd Identification. Cambridge University Press. Second edition 1990, pp. 595–597.

Wei X. Use of yeast for bioenrichment with germanium. Shipin Kexue (Beijing) 1992, 149, 49–54, 39.

Babeva et al. Methods for Isolation and Identification of Yeasts. Publishing House"Food Industry" Moscow 1979, pp. 9–18.

Puempel et al., "Silver tolerance and silver accumulation of microorganisms from soil material s of a silver mine", Appl. Microbiol Biotechnol., 1986, 24 (3), pp. 244–247.

Brock et al. "Enrichment Culture", In: Biology of Microorganisms. Fourth Edition, 1984, Prentice–Hall. Inc., Englewood Cliffs, NJ, pp. 617–619.

*Primary Examiner*—Sandra E. Saucier
*Assistant Examiner*—Vera Afremova
*Attorney, Agent, or Firm*—Lyon & Lyon LLP

[57] ABSTRACT

The present invention includes a novel yeast strain of the genus *Saccharomyces boulardii* sequela PY31 ATCC 74366 that is able to process certain metallic compounds into biologically active forms suitable for supplementing the human diet. The present invention also includes methods for isolating such yeast, nutritional supplement compositions containing such yeast, and methods of administering the nutritional supplement compositions to humans.

15 Claims, No Drawings

ORGANOMETALLIC-METABOLIZING YEAST

BACKGROUND OF THE INVENTION

1. Field of the Invention

This invention relates to the field of human dietary supplements, and more specifically to a novel yeast strain of the genus *Saccharomyces boulardii* sequela which has the ability to process certain metallic compounds into forms that are biologically active and useful in supplementing the human diet.

2. Background of the Invention

Metal supplementation of the human diet is generally recognized as an important area in the field of nutritional science. Although no "RDA" minimum daily intake requirements have been officially adopted, research has strongly suggested that absence of some minerals, particularly metallic minerals such as chromium, germanium, and selenium, can lead to improper functioning of the body's metabolic processes, and a host of diseases and disorders. For example, selenium has been implicated as a mineral that may affect a reduction in the incidence of certain cancers when ingested in amounts of about 50 µg. [W. Blott et al., *J. Natl. Cancer Institute*, 85(18):1483–92 (1993); H. P. Leis, *Int. Surg.*, 76:1–5 (1991)]. Chromium is believed to play a role in modulating the symptoms of diabetes. [G. Mahdi and D. Naismith, *Ann. Nutr. Metab.*, 35:65–70 (1991)].

Nutritional supplementation of the human diet with metals, using inorganic or organometallic sources for the metals, has met with limited success. Safety and efficacy in the human metabolism of such metals has been questioned, since most inorganic forms of metals are know to have appreciable toxicity. For example, selenium is usually administered as selenium trioxide species—an agent which is extremely toxic. Trivalent chromium has been administered as inorganic chromium, typically chromium chloride or chromium acetate, or as organometallic species such as chromium picolinate or chromium nicotinate, but each of these forms of chromium has been shown to be toxic in one fashion or another, reflecting a major shortcoming in their use in nutritional supplements. In addition, inorganic forms of such metals generally have a low bioavailability, making their use in nutritional supplements questionable.

Supplementation of the human diet with metal-enriched yeast products has been sought as an alternative. Potential advantages of administering a metal derived from yeast as a nutritional supplement over non-yeast derived forms are that the toxicity of the metal will be lower in yeast-derived organometallic compounds, and that since yeast-derived organometallic compounds are more soluble, such compounds will be better metabolized by the human body. However, a drawback of using yeast-derived metallic material as a food supplement is that rather large amounts of yeast are usually needed in order to acquire the proper dosage, since the levels of metal ion produced in yeast typically range from about 500 to 2000 ppm (µg/g)—levels which would require ingestion of large amounts of yeast if the nutritional benefit of the organometallic compounds is to be realized.

3. Description of the Prior Art

Skogerson, U.S. Pat. No. 4,348,483, discloses a method for producing chromium-enriched yeast by incubating yeast in an aqueous solution of inorganic chromium salts, such as $CrCl_3$, with growth media. Although the chromium content of the yeast is about 500 to 1000 ppm, the process entails, to a large degree, internalization of chromium without metabolization of the inorganic chromium salt so that there is a high probability that a significant, if not all the chromium found in the chromium-enriched yeast is inorganic chromium. Hence, to the extent that the chromium produced in this process is merely trivalent chromium salts mixed with the structural material of yeast, the chromium produced using this method does not possess high bioactivity and is also toxic if ingested in high doses.

Szalay, U.S. Pat. No. 4,343,905, teaches a method of concentrating chromium in Brewer's yeast by cultivating the yeast in a broth where the source of trivalent chromium is from a mixture of chromium oxide and certain amino acids. Although this method yields yeast with an intracellular chromium concentration of about 2000 ppm, 80% of which is reported to as yeast-metabolized chromium, this method encounters difficulties due to the insolubility of the chromium oxide. Also, similar to U.S. Pat. No. 4,348,483, internalization without metabolization of the chromium oxide is highly probable, and will likely result in chromium oxide, known to have appreciable toxicity to the human system, remaining in its toxic form.

The isolation and selection of a particular strain of Vietnamese yeast for assimilating about 300 ppm selenium metal is known. [Dang Hong Thuy, et al., *Tap Chi Duoc Hoc*, (4):9–12 (1992)]. Assimilation of inorganic selenium by Brewer's yeast, when grown in the presence of 150 ppm selenium trioxide disodium salt, produced a yeast product having about 1000 ppm selenium, and where about 3% of this was inorganic selenium, about 30% was selenoamino acids, and the remainder was present as other yeast-derived organoselenium compounds. [Xie, L. et al., *Weishenwu Xuebao*, 30(1) :36–40 (1990)].

A method for preparing yeast-derived germanium has been taught by Komatsu, Japanese Patent 77-46138770420. However, this method involves the preparation of germanium yeast using a highly toxic form of germanium, $GeO_2$, as the source of germanium for the feed and cultivation of the yeast. The major shortcoming of this method is it results in an appreciable content of non-metabolized $GeO_2$ by-product. Since $GeO_2$ is a highly toxic agent, this method is not useful as a dietary supplementation for the human diet.

There remains a need for novel yeast strains that metabolize metal ions to provide a non-toxic yeast product that provides a form of the metal that is highly metabolizable by the human system and that is of sufficient concentration so that the product is suitable for the commercial marketplace for nutritional supplements.

SUMMARY OF THE INVENTION

The present invention overcomes the shortcomings of the prior art by providing methods for isolating and culturing a novel yeast strain of *Saccharomyces boulardii* sequela, and for using that yeast strain as a biological source for producing forms of metal ions that are non-toxic and highly metabolizable by the human body, and which are useful for supplementation of the human diet. This discovery is based on a process for isolating and purifying the novel yeast strain comprising the steps of:

(a) selecting an appropriate location to collect fertile samples containing the desired yeast strain;

(b) sampling the soil to insure the desired yeast species is present;

(c) isolating the yeast strains of the soil sample;

(d) screening the yeast;

(e) cultivating the yeast;
(f) storing of the yeast; and
(g) producing organometallic compositions using the yeast.

Hence, it is an object of the present invention to provide a method for isolating, cultivating the pure yeast strain *Saccharomyces boulardii* sequela PY31—a novel strain of *Saccharomyces boulardii* sequela.

It is another object of the present invention to provide a biosynthetic method which employs yeast strain *Saccharomyces boulardii* sequela PY31 in preparing organometallic complexes with high biological activity.

It is a further object of the present invention to provide improved forms of metal ions (included in a dried yeast product) that are derived from yeast strain *Saccharomyces boulardii* sequela and that are non-toxic and highly metabolizable by the human body.

It is still another object of the present invention to provide a method for the production of chromium-enriched yeast, where the source of chromium for metabolism by the yeast is a trivalent chromium chelate complex of niacin and glycine, and where the yeast source is *Saccharomyces boulardii* sequela PY31.

It is another object of the present invention to provide a yeast strain that will assimilate germanium metal and provide a product that is non-toxic to the human system and a form of germanium that is highly metabolizable by the human system.

It is a further object of the present invention to provide a yeast strain that will assimilate selenium metal and provide a product that is non-toxic to the human system and a form of selenium that is highly metabolizable by the human system.

It is yet a further object of the present invention to administer the dried yeast product of the present invention to humans to promote good nutritional health.

It is still another object of the present invention to provide forms of metal ions that are non-toxic to the human body and, when used as food supplements, reduce the susceptibility of the human body to chronic disorders, such as heart disease, diabetes, and possibly cancer.

DETAILED DESCRIPTION OF THE INVENTION

The present invention relates to the isolation and purification of a new strain of Baker's (or Brewer's) yeast, *Saccharomyces cerevisiae*, and to certain methods of cultivating this new strain of yeast that yields dried yeast mass having an enriched content of the metal ion where the form of this metal ion engenders high biological activity, and to uses of such as a nutritional supplement for the human diet. Specifically, *Saccharomyces cerevisiae* and *Saccharomyces boulardii* sequela are of the same genus, and *Saccharomyces boulardii* sequela is described as a synonym of *Saccharomyces cerevisiae*. [Barnett et al., *Yeasts: Characteristics and Identification*, Cambridge Univ. Press (1990)].

More particularly, the present invention teaches a method for isolating a novel yeast strain of *Saccharomyces boulardii* sequela from raw soil samples, and cultivating it to yield quantities of yeast at a scale sufficient for developmental research and for production of commercial products. The novel strain of yeast of the invention, *Saccharomyces boulardii* sequela PY31 has been deposited in an International Repository in accord with the Budapest Treaty and has been assigned ATCC No. 74,366. American Type Culture Collection, 10801 University Boulevard, Manassas, Va. 20110-2209.

Specifically, the method for isolating a novel yeast strain of the present invention comprises:
(1) identifying a location for collection of a soil sample, which is proximal to a germanium mine (i.e., within 100 yards of a germanium mine);
(2) sampling the soil by removing about 200 g from a depth of 5 cm to 20 cm, and transporting the sample using a sterilized bag;
(3) growing the living material on three different mediums which support the growth of all yeast, each that selectively kills bacteria without killing the yeast;
(4) separating the yeast from other living matter and then repeating this process until yeast can be grown without bacterial contaminants;
(5) selecting and restreaking the yeast colonies, and repeating this process three times;
(6) selecting the yeast colonies most vital for growth in a medium enriched with germanium;
(7) growing the selected colonies each on malt extract agar or dextrose agar, and selecting which colonies appear most robust, and;
(8) cultivating the selected yeast by growing 1–2 slants of the yeast for about 2 days at about 30° C. and then transferring to the cultivated yeast about 100 mL of malt extract broth and then incubating at about 30° C. for 8–10 hours, then adding to the incubated mixture about 500 mL of malt extract broth and then growing the resulting mixture at about 30° C. overnight.

The present invention also includes a process for producing an organometallic yeast product which comprises the steps of:
(1) preparing a solution of the metal ion in warm distilled water and then filtering;
(2) adding the live yeast culture of the isolated yeast strain *Saccharomyces boulardii* sequela PY31 and incubating as a mixture with the metallic ion with gentle shaking action for about 90 minutes;
(3) adding yeast growth nutrients and incubating at about 30° C. for about 24 hours;
(4) recovering and concentrating the yeast cells from the aqueous growth media;
(5) washing the recovered yeast cells to remove extracellular unprocessed metallic species; and
(6) pasteurizing and drying the washed yeast cells.

The present invention teaches a use of the novel yeast strain *Saccharomyces boulardii* sequela PY31 for preparing metal-enriched yeast forms. For example, the present invention has been used to prepare a germanium-enriched yeast product that has a high intracellular content of organically bound germanium in a form that is highly metabolizable by the human system and that is non-toxic to the human system. The method of this invention which comprises contacting live yeast cells in a aqueous suspension of dicarboxyethylgermaniumsesquioxide at levels between 1,000 ppm and 20,000 ppm, and preferably between 10,000 ppm and 20,000 ppm, and most preferably 20,000 ppm of the dicarboxyethylgermaniumsesquioxide, under controlled pH of about 4.2 to about 5.5, and preferably about 4.8 to about 5.3, and most preferably between about 4.9 and about 5.2, and temperature from about 20° C. to about 35° C., preferably 28° C. to 32° C. Then, the yeast and germanium mixture is incubated for about 5 minutes to about 120 minutes, preferably about 20 minutes to about 100 minutes, and most preferably about 90 minutes, and then growth media is added to induce growth, followed by incubating the resulting suspension with shaking at about 200 rpm for a period of at least about 10 hours, preferably from about 15 hours to about 60 hours, and most preferably about 24 hours, at a temperature of about 25° C. to about 35° C., and preferably about 30° C. The mixture is then centrifuged at about 3,500 rpm for about 10 minutes, the solid isolated and washed with the solvent to rid completely of extracellular germanium. The resultant mixture is pasteurized and dried to produce a dry yeast product.

The present invention also has been used for preparing a chromium-enriched yeast product that has a high intracellular content of organically bound trivalent chromium in a form, or forms, which are highly biologically active and non-toxic. The method for preparing the chromium-enriched yeast comprises contacting live yeast cells (*Saccharomyces boulardii* sequela PY31) in an aqueous suspension of chromium chelate complex of chromium glycinate dinicotinate at levels between about 200 ppm and about 20,000 ppm chromium complex, and preferably about 500 ppm to about 15,000 ppm and most preferably about 7,500 ppm to about 10,000 ppm of the chromium complex, under controlled pH of about 4.2 to about 6.0, and preferably from about 4.5 to about 5.3, and temperature from about 20° C. to 35° C., preferably 28° C. to 32° C. The resultant mixture is incubated for about 5 minutes to about 120 minutes, preferably about 20 minutes to about 95 minutes, and most preferably about 90 minutes, and then growth media is added to induce growth, followed by incubation of the resulting suspension with shaking at about 200 rpm for a period of at least about 10 hours, preferably from about 15 hours to about 60 hours, and most preferably about 20 hours, at a temperature of about 25° C. to about 35° C., and preferably about 30° C. The resultant mixture is then centrifuged at about 3,500 rpm for about 10 minutes, the solid isolated and washed with the solvent to rid the mixture completely of extracellular chromium. The resultant mixture is then pasteurized and dried to produce a dry yeast product.

The present invention may also be used to prepare a selenium-enriched yeast product that has a high intracellular content of organic selenium in a form which is highly biologically active and substantially non-toxic. The process for obtaining the selenium-enriched yeast product is analogous to the process for obtaining the germanium and chromium-enriched yeast products and is believed to be within the ordinary skill in the art. Indeed, the above-described process may be used to assimilate other organometallic compounds which are known to be necessary to the human diet.

To prepare the yeast compositions of the invention for use as a dietary supplement, the yeast product is combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent advantageous oral dosage unit forms, in which cases solid pharmaceutical carriers are obviously employed. If desired, tablets may be sugar coated or enteric coated by standard techniques.

For parenteral products the carrier will usually comprise sterile water, although other ingredients may be included, e.g., to aid solubility or for preservation purposes. Injectable suspensions may also be prepared, in which case appropriate liquid carriers, suspending agents, adjuvants, and the like may be employed.

A composition of the present invention is generally effective when parenterally administered in amounts ranging from about 50 $\mu$g/dose (1 dose per body weight of about 75 kg) to about 200 $\mu$g/dose of composition. This is equivalent to about 5 mg/dose to about 1 g/dose of the dried yeast germanium-containing product. When orally administered, the compositions of the present invention are generally effective in approximately the same amounts as the parenteral products. Activity at this level makes the compositions particularly well suited for formulations in tablet size for oral administration. The above dosage ranges are likely to be administered at varying periods for humans, for example, from daily administration to administration at least 5 times per week. However, ultimately, the dosage regiment will depend upon the particular needs of the user.

The following examples are illustrative only and do not limit the invention in any fashion.

EXAMPLE 1

Yeast strain *Saccharomyces boulardii* sequela PY31 was isolated and purified as follows. Soil samples were collected (about 200 g per sample) from a depth of about 5 cm to about 20 cm, at a location near a germanium mine proximal to St. George, Utah. The sampling occurred in the daytime, close to where mineral aggregates could be observed and as moist as possible, where a temperature of about 28° C. to about 30° C. and a pH of the soil between about 5.5 to about 6.0 were measured. The samples were stored in a sterilized bag at about 5° C. (ice chest). The samples were then secured within the laboratory within 1–2 days, and were processed a few hours after being so secured. About 1 g of each sample (a total of 10 samples was collected) was added to about 99 g of malt broth (pH 7.4) or lactose broth (pH 6.9 [DIFCO]), and this was shaken at 200 rpm for 1 hour.

The yeast colonies that were the fastest growing colonies were selected as follows. Serial dilutions (10 fold) were made and each dilution was streaked onto an agar plate and incubated. From these plates, a dilution that gave rise to a separate and independent colony of cells that grew well was identified. After the yeast colonies developed fully, they were carefully inspected with a microscope, and one colony of each morphological type was picked and purified by replating on to three types of agar that support yeast growth but inhibits the growth of bacteria. Specifically, several types of growth media were used: malt extract agar (pH 4.7 [DIFCO]) with 0.1% chlorophenicol or ampicillin (50 $\mu$g/L), Sabouraud dextrose agar (pH 5.6 [DIFCO]) with 0.1% chlorophenicol or ampicillin (50 $\mu$g/L), and potato dextrose agar (pH 5.6 [DIFCO]) with 0.1% chlorophenicol or ampicillin (50 $\mu$g/L). Each of these agar plates contained a substance that kills bacterial contaminants. The isolated yeast strain was streaked onto each of the three different types of agar plates.

The colonies were counted after 2–7 days of incubation at 28° C. The colonies that appeared to be the most well formed [See, e.g., Colom'e J. S., et al., *Laboratory Exercises in Microbiology*, West Publishing Co. 68–69 (1986)] were selected and were restreaked, and this procedure was repeated at least 3 times.

The yeast strain *Saccharomyces boulardii* sequela PY31 was selected based on its superior vitality when grown in the presence of an organogermanium species (dicarboxyethylgermaniumsesquioxide) and germanium dioxide, and this was carried out as follows. A 100:1 dilution of actively growing yeast culture (isolated as per the protocol described above) was made, and about 10 mL aliquots were added to 20 mL test tubes containing 10,000 ppm dicarboxyethylgermaniumsesquioxide, and to a 20 mL test tube containing about 50 ppm of germanium dioxide, and these were each incubated at about 30° C. for 2 days. The increase in absorbance (which reflects total yeast density and, therefore, the total amount of yeast) was measured by monitoring the optical density at 590 microns ($OD_{590}$) [Beckman DU 460]. Two different types of germanium were tested for incorporation into the novel yeast strain. Specifically, germanium sesquioxide is an organic form of germanium that is not toxic to humans, while germanium dioxide is an inorganic compound and is highly toxic to humans. Although both forms of germanium were tested, since certain strains of yeast find germanium dioxide toxic, and since the low solubility of germanium dioxide limits the exposure levels for the yeast culture to germanium, the present invention uses germanium sesquioxide as the form of germanium in the culture media.

These selected yeast cultures were streaked on malt extract agar and potato dextrose agar and selected the colonies that were the most well-formed. The yeast strain *Saccharomyces boulardii* sequela PY31 was chosen as far superior in the ability to grow under the above-described conditions, from malt extract agar with ampicillin. Yeast strain *Saccharomyces boulardii* sequela is characterized by a creamy, non-mucoid, slightly raised colonies and budding cells. This yeast grows well in the presence of germanium. The yeast strain *Saccharomyces boulardii* sequela PY31 was cultivated by subjecting one to two slants of the yeast to incubation at 25° C. to about 30° C. for 2 days and transferred the resulting culture to 100 mL of malt extract broth (pH 4.7 [DIFCO]), and then this was incubated at about 30° C. for 8–10 hr, and then 500 mL of malt extract broth was added and this was incubated at 30° C. overnight. The growth of the cells was monitored by checking the $OD_{590}$ and counting the number of yeast cells under the microscope. This yeast product can be used directly for the cultivation and harvesting of metal-enriched yeast.

EXAMPLE 2

This example describes a procedure to produce a germanium-enriched yeast using the novel yeast strain of the present invention. The yeast strain *Saccharomyces boulardii* sequela PY31 was cultivated and harvested in a pure form as follows. One slant of yeast was incubated for two days at 30° C., and then grown in 200 mL of Malt extract at 30° C., shaken at 200 rpm for 8 hrs, and then to this was added 300 mL of malt extract and the resulting mixture was incubated at 30° C. overnight. A stock solution (10,000 ppm) of dicarboxyethylgermaniumsesquioxide was prepared as follows. To 300 mL of distilled water at ambient temperature was added 3.0 g of dicarboxyethylgermaniumsesquioxide [Westar Nutrition Inc.] and the resulting mixture was warmed to 40–60° C., were it was maintained for 1 hour. The pH of the cooled homogeneous solution was adjusted to 5.2 and then this was filtered through cellulose acetate membrane [Corning].

The growth medium was prepared as follows. 79° Brix molasses (670 g) [TCT, Gold Coast] was diluted to 1 L with distilled water, then 2.72 g of KCl was added, followed by 2.72 g of $MgSO_4.7 H_2O$ and then 29.28 g of $NH_4H_2PO_4$, and this was stirred to homogeneity. To this was added enough water to reach a final volume of 2 L (25° Brix molasses solution). The mixture was tested for sugar content by using a hydrometer, final pH is 5.0. This was subjected to autoclave at 121° C. for 15 minutes. The yeast were cultivated as follows. To 250 mL of the stock dicarboxyethylgermaniumsesquioxide solution was added 30 mL of yeast strain *Saccharomyces boulardii* sequela PY31 and the resulting suspension was shaken for 90 minutes, and then 60 mL of 25° Brix molasses solution was added and the resulting mixture was shaken at 200 rpm for 24 hours at 30° C. This mixture was centrifuged at 3,900 rpm for 10 minutes, the supernatant removed, then the yeast cells were washed once with 100 mL, of 0.1M EDTA (pH=7.8), and 0.01 M $Na_2HPO_4$ buffer solution, and then four times with 100 mL of distilled water. The resulting yeast cream was dried in vacuo and then the germanium content of the yeast was measured using atomic absorption techniques. To accomplish this measurement, 0.5 g of the dried yeast sample is transferred to a 50 mL volumetric flask. To the flask, 5 mL of concentrated $HNO_3$ is added and left overnight. The flask is then placed in a boiling water bath for four hours under a hood. After the flask is removed and has cooled, distilled water is added in sufficient amount to fill the flask to its 50 mL line. The resultant solution is then filtered through #2 Whatman filter paper into a round bottom flask. About 10 mL of the sample is then measured for its germanium content using an atomic absorption spectrometer [Beckman Instruments] set at a wavelength of 265.7 nm, a slit width of 0.2 nm, and a germanium lamp current at 35 mA. The final concentration of germanium was 5,404 ppm.

EXAMPLE 3

This example describes a procedure to produce a germanium-enriched yeast using the novel yeast strain of the present invention. The yeast strain *Saccharomyces boulardii* sequela PY31 was cultivated and harvested in a pure form as follows. One slant of yeast was incubated for two days at 30° C., and then grown in 240 mL of 2.4% potato dextrose broth at 30° C., shaken at 200 rpm for 8 hrs, and then to this was added 240 mL of 2.4% potato dextrose broth and the resulting mixture was incubated at 30° C. overnight. A stock solution (10,000 ppm) of dicarboxyethylgermaniumsesquioxide was prepared as follows. To 300 mL of distilled water at ambient temperature was added 3.0 g of dicarboxyethylgermaniumsesquioxide [Westar Nutrition Inc.] and the resulting mixture was warmed to 40–60° C., were it was maintained for 1 hour. The pH of the cooled (about 25° C.) homogeneous solution was adjusted to about 5.1 and then this was filtered through cellulose acetate membrane [Corning].

The growth medium was prepared as follows. 79° Brix molasses (670 g) [TCT, Gold Coast] was diluted to 1 L with distilled water, then 2.72 g of KCl was added, followed by 2.72 g of $MgSO_4.7 H_2O$ and then 29.28 g of $NH_4H_2PO_4$, and this was stirred to homogeneity. To this was added enough water to reach a final volume of 2 L. The mixture was tested for sugar content by using a hydrometer, final pH is 5.0. This was subjected to autoclave at 121° C. for 15 minutes.

The yeasts were cultivated as follows. To 250 mL of the stock dicarboxyethylgermaniumsesquioxide solution was added 250 mL of yeast strain *Saccharomyces boulardii* sequela PY31 and the resulting suspension was shaken for 120 minutes, and then 35 mL of 20% glucose solution was added and the resulting mixture was shaken at 200 rpm for 16 hours at 30° C. This mixture was centrifuged at 3,900 rpm for 10 minutes, the supernatant removed, then the yeast cells were washed once with 100 mL of 0.1M EDTA (pH=7.8) and 0.01 M Na$_2$HPO4 buffer solution, and then four times with 100 mL of distilled water. The resulting yeast cream was dried in vacuo and then the germanium content of the yeast was measured using atomic absorption techniques. To accomplish this measurement, 0.55 g of the dried yeast sample is transferred to a 50 mL volumetric flask. To the flask, 5 mL of concentrated HNO$_3$ is added and left overnight. The flask is then placed in a boiling water bath for four hours under a hood. After the flask is removed and has cooled, distilled water is added in sufficient amount to fill the flask to its 50 mL line. The resultant solution is then filtered through #2 Whatman filter paper into a round bottom flask. About 10 mL of the sample is then measured for its germanium content using an atomic absorption spectrometer [Beckman Instruments] set at a wavelength of 265.7 nm, a slit width of 0.2 nm, and a germanium lamp current at 35 mA. The final concentration of germanium is 1,418 ppm.

Numerous modifications and variations of the present invention are included in the above-identified specification and are expected to be obvious to one of skill in the art. It is also intended that the present invention cover modifications and variations of the compositions and method for using them to accomplish their claimed uses within the scope of the appended claims and their equivalents.

We claim:

1. A biologically pure culture of *Saccharomyces boulardii* ATCC 74,366 or an organometal metabolizing mutant thereof.

2. A method for producing a biologically pure culture of claim 1, comprising the steps of:
   isolating yeast strain *Saccharomyces boulardii* ATCC 74,366, or a strain of *S. boulardii* having all of the identifying characteristics of ATCC 74,366, from a soil sample; and
   purifying the isolated yeast strain.

3. The method as set forth in claim 2, wherein the isolating step comprises the steps of:
   selecting an appropriate location to collect the soil sample;
   collecting the soil sample; and
   evaluating the soil sample to insure the presence of the yeast strain.

4. The method as set forth in claim 3, wherein the location is within 100 yards of a germanium mine.

5. The method as set forth in claim 3, wherein the collecting step comprises the steps of:
   removing approximately 200 grams of soil from a depth of about 5 centimeters to about 20 centimeters; and
   placing the removed soil into a sterile container.

6. The method as set forth in claim 3, wherein the isolating step further comprises the steps of:
   growing living material from the removed soil on each of a plurality of growth media, wherein each growth medium supports yeast growth and kills bacteria without killing yeast;
   separating the grown yeast from other living matter;
   repeating the growing and separating steps until yeast can be grown, in at least one of the plurality of growth media, without bacterial contaminants; and
   selecting, from among the grown yeast, the isolated yeast strain.

7. The method as set forth in claim 2, wherein the purifying step comprises the steps of:
   growing colonies of the isolated yeast strain on an agar selected from the group comprising malt extract agar and dextrose agar;
   selecting robust colonies from the grown colonies; and
   cultivating the selected robust colonies.

8. The method as set forth in claim 7, wherein the cultivating step comprises the steps of:
   growing at least one slant of the selected robust colonies for about two days at about 30° C.;
   transferring the grown slant to about 100 mL of malt extract broth to form a first mixture;
   incubating the first mixture for about 8 to about 10 hours at about 30° C.;
   adding about 500 mL of malt extract broth to the incubated first mixture to form a second mixture; and
   incubating the second mixture for about 8 hours to about 16 hours at about 30° C.

9. A method for preparing an organometallic yeast product comprising:
   selecting a soil sample by a method selected from the group consisting of obtaining soil within 100 yards of a germanium mine and obtaining soil from a site having visually observable germanium metal aggregates;
   collecting the soil sample;
   evaluating the soil sample to insure the presence of a Saccharomyces yeast strain which is capable of growing in a culture medium comprising about 6600 ppm dicarboxyethyl germanium sesquioxide;
   separating the Saccharomyces yeast from the soil sample;
   growing the Saccharomyces yeast in a growth medium to create a yeast culture;
   adding a solution comprising a metal ion to yeast cells of the yeast culture;
   pasteurizing the yeast cells; and
   drying the pasteurized yeast cells to obtain the organometallic yeast product.

10. The method of claim 9 wherein the soil sample is collected at a depth of 5 cm to 20 cm.

11. The method of claim 9 wherein the soil sample is collected at a temperature of 28° C. to 30° C.

12. The method of claim 9 wherein the soil sample is collected at a pH of 5.5 to 6.0.

13. The method of claim 9 wherein the solution comprising a metal ion comprises a germanium ion.

14. The method of claim 13 wherein the germanium ion is germanium sesquioxide.

15. The method of claim 9 wherein the solution comprising a metal ion comprises an ion of selenium.

* * * * *